United States Patent
Yang

(10) Patent No.: US 9,925,226 B2
(45) Date of Patent: Mar. 27, 2018

(54) METHOD FOR MANUFACTURING WATER-SOLUBLE MEDICAL AMBER CRYSTALS

(71) Applicant: Huei Chen Yang, Taipei (TW)

(72) Inventor: Huei Chen Yang, Taipei (TW)

( * ) Notice: Subject to any disclaimer, the term of this patent is extended or adjusted under 35 U.S.C. 154(b) by 854 days.

(21) Appl. No.: 14/328,725

(22) Filed: Jul. 11, 2014

(65) Prior Publication Data
US 2016/0008418 A1    Jan. 14, 2016

(51) Int. Cl.
*A61K 36/00*    (2006.01)

(52) U.S. Cl.
CPC .......... *A61K 36/00* (2013.01); *A61K 2236/00* (2013.01)

(58) Field of Classification Search
CPC ..................................................... A61K 36/00
USPC ........................................................ 424/725
See application file for complete search history.

(56) References Cited

U.S. PATENT DOCUMENTS 6,545,016 B1 *    4/2003    Dellaria ............... C07D 471/04
                                                                  514/303

\* cited by examiner

*Primary Examiner* — Michael V Meller

(57) ABSTRACT

A method for manufacturing water-soluble medical amber causes that original great molecular groups of medical amber crystals are decomposed into hydrophilic extracted liquid plentiful of water and having small molecular groups, which can be directly coated on skin without mixing with water and added with grease or oil. The method original performs disinfecting and sterilizing treatment for natural medical amber crystals; after a polishing and cleaning step, they are placed in a bottle with treatment liquid therein for a predetermined time period so that the mixture in the bottle ferments and decomposes into small pieces which presents as cream-like liquid. Then paddies are added into the bottle. The bottle is retained through several months so that the medical amber crystals ferment quickly to form as a liquid composite. Then the bottle is evaporated several hours so that the liquid composite is distilled out of the bottle.

1 Claim, 1 Drawing Sheet

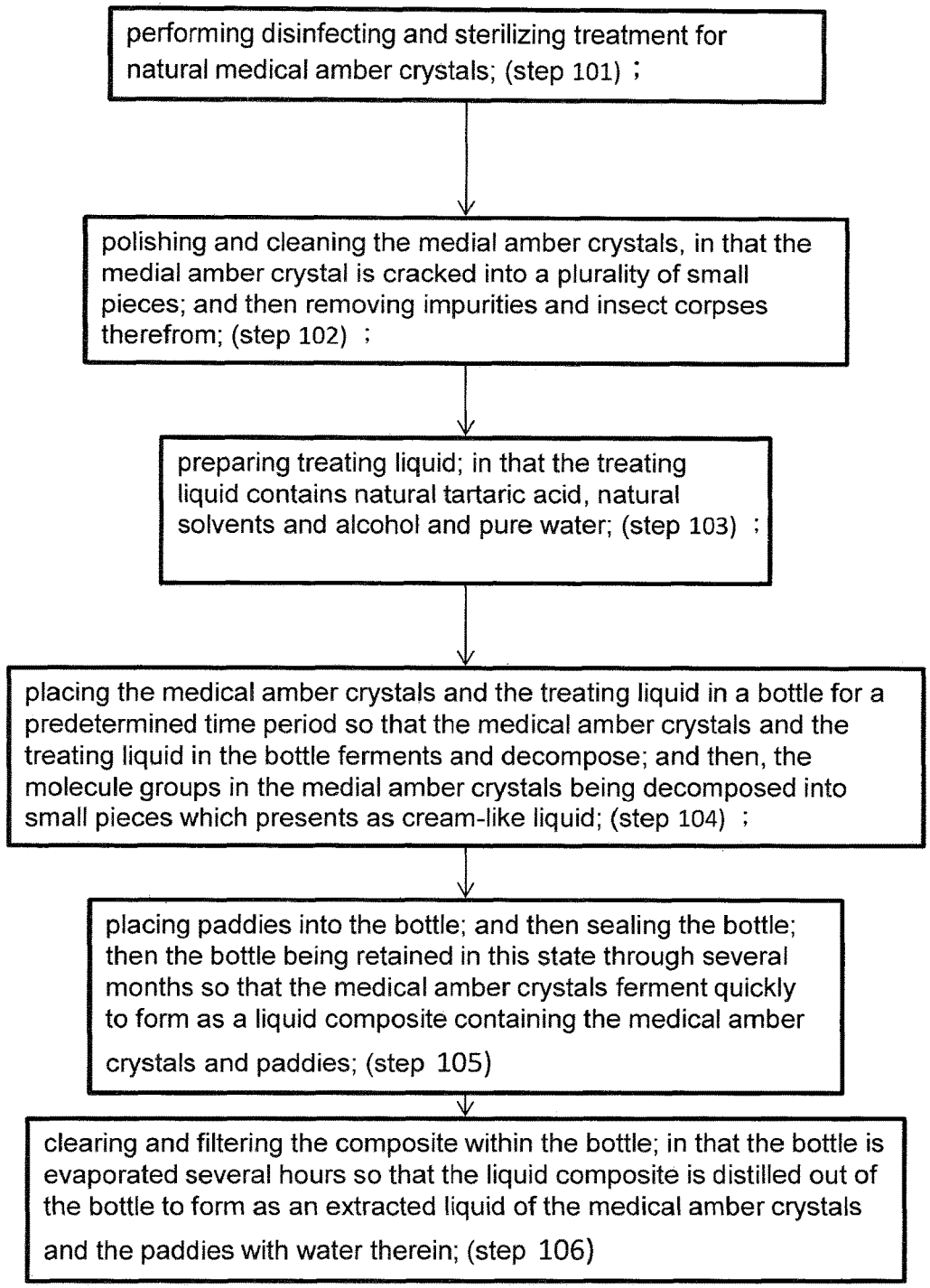

METHOD FOR MANUFACTURING WATER-SOLUBLE MEDICAL AMBER CRYSTALS

FIELD OF THE INVENTION

The present invention related to treatment of medical amber crystals, and in particular to a method for manufacturing water-soluble medical amber crystals.

BACKGROUND OF THE INVENTION

Medical amber crystals are a kind of resin flowing from trees and are buried under earth through several thousand years. The crystals are organic fossils, which is a kind of organic mineral. Generally, medical amber crystals have various kinds with different colors. The surfaces thereof are formed with textures due to the flow of resin. Furthermore, bubbles. insect corpses and plant debris are remained therein.

General used medical amber crystals are dark ambers or daemonorops draco. BL. which originally are resins exuded from Dracaena (dragon's blood tree) and are widely used in medicines or as gemstones. The records about these materials in history are begun from one thousand years ago. Generally, these ambers color are red, dark red or black, depends on years.

A few of notable facts about amber's use as medicine are recorded as following. Ancient Romans believed that amber possessed medicinal qualities. Hippocrates (460-377 BC), father of medicine, in his works described medicinal properties and methods of application of amber that were later used by scientists until the Middle Ages. In ancient Rome, Amber was also used as a protection against different diseases. Cali stratus, famous physician of those times, wrote that amber protects from madness, powder of amber mixed with honey cures throat, ear and eye diseases and taken with water cures stomach illnesses.

Medicinal Attributes of the amber crystals are that astringent for diarrhea, antibacterial, used to treat wounds and invigorate the blood. Medicinal: The resin of Dragon's Blood is used externally as a wash to promote healing and stop bleeding. Internally it is used for chest pains, postpartum bleeding, internal traumas, and menstrual irregularities. Dragons Blood Meridian: heart, liver dispel blood stasis, relieve pain, traumatic injuries causing fractures, contusion, sprains, bruising and stops bleeding (topically) protect decay of ulcer surface, generate flesh, chronic non-healing sores.

However, conventionally, the medical amber crystals are not hydrophilic and thus it cannot be resolved in water. As a result, as coating the crystal on skin, some greased or oil material must be added thereto so as to make the crystals be absorbed by the skin. This action induces some inconvenient to users and thus the reduction of the use of medical amber crystals.

SUMMARY OF THE INVENTION

Accordingly, to resolve above mentioned problem, the present invention provides a method for manufacturing water-soluble medical amber, wherein a complicated process and a strictly operation environment are provided so that original large molecular groups of medical amber crystals are decomposed into hydrophilic extracted liquid of medical amber crystals plentiful of water and having small molecular groups, which can be directly coated on skin without mixing with water and added with grease or oil. The defect in the prior art medical amber crystals is overcome. The present invention has overcome the defect of the conventional medical amber crystals, which can be resolved in water. Therefore, the usages of the medical amber crystals are widened.

To achieve above object, the present invention provides a method for manufacturing water-soluble medical amber comprising the following steps of: performing disinfecting and sterilizing treatment for natural medical amber crystals; polishing and cleaning the medial amber crystals, in that the medial amber crystal is cracked it into a plurality of small pieces; and then removing impurities and insect corpses therefrom; preparing treating liquid; in that the treating liquid contains natural tartaric acid, natural solvents and alcohol and pure water; placing the medical amber crystals and the treating liquid as a mixture in a bottle for a predetermined time period so that the mixture in the bottle ferments and decompose; after decomposition, the molecule groups in the medial amber crystals being decomposed into small pieces which presents as cream-like liquid; opening a cover of the bottle and placing paddies into the bottle; and then covering the bottle; then the bottle being retained in this state through several months so that the medical amber crystals ferment quickly to form as a liquid composite containing the medical amber crystals and paddies; at this time, debris of the medial amber crystals and paddies sunk at on a bottom side of an interior of the bottle are removed; only the composite at an upper side is remained; and clearing and filtering the composite within the bottle; in that the bottle is evaporated several hours so that the liquid composite is distilled out of the bottle to form as an extracted liquid of the medical amber crystals and the paddies with water therein; wherein the extracting liquid contains amber cream and nutrient of the paddies, and thus it has plentiful of vitamins A and E, tocopherols.

BRIEF DESCRIPTION OF THE DRAWINGS

FIG. 1 is a flow diagram showing the process of the present invention.

BRIEF DESCRIPTION OF THE INVENTION

In order that those skilled in the art can further understand the present invention, a description will be provided in the following in details. However, these descriptions and the appended drawings are only used to cause those skilled in the art to understand the objects, features, and characteristics of the present invention, but not to be used to confine the scope and spirit of the present invention defined in the appended claims.

With reference to FIG. 1, the method for manufacturing water-soluble medical amber crystal according to the present invention is disclosed, in that the medical amber crystal is especially for dark ambers or daemonorops draco. BL. With reference to FIG. 1, the method comprises the following steps of:

Evaporating natural medical amber crystals (step 101) in a bamboo-basin; in that a water pan is placed below the basin; the water pan is heater by fire so that liquid within the pan is heated and then evaporates. The vapor from the water will flow into the bamboo-basin and then permeate into the medical amber crystals, wherein the liquid in the water pan is water mixing with natural plants. The object for evaporation is to kill bacteria therein. The time for evaporation is about 3 hours each time and the process is performed several times, preferable over 3 times (step 1012).

Polishing and cleaning the medial amber crystals, in that the medial amber crystal is taken out from the bamboo basin and cracking it into a plurality of small pieces; and then removing impurities and insect corpses therefrom (step 102);

Preparing treating liquid; in that the treating liquid contains natural tartaric acid, natural solvents and alcohol and pure water; wherein the natural solvent is such as pine root solution (step 103);

Placing the medical amber crystal and the treating liquid in a bottle for a proper time period so that the mixture in the bottle ferments and decompose. Originally, the ratio of medical amber crystals is about 25% to 35%, the ratio of the natural tartaric acid is about 5% to 8%; the ratio of natural solvent is about 5% to 8%, the ratio of alcohol is about 25% to 35% and the ratio of pure water is about 30% to 40%.

After decomposition, the molecule groups in the medial amber crystals are decomposed into small pieces which presents as cream-like liquid (step 104). Preferably, the bottle is placed in an environment having temperature about 18° C. to 28° C. and is radiated with proper light with predetermined light intensities through a time period about six months. Therefore, the original solid-state medial amber crystals decompose into cream-like liquid. Preferably, the bottle is a ceramic bottle or glass bottle.

Opening a cover of the bottle and placing paddies into the bottle; and then covering the bottle; then the bottle being retained in this state through a period of 1 to 4 months (step 105). Preferably, the paddies are newly paddies which are just taken out from ears of rice (or spikes of rice) with a time period not over 24 hours so that the medical amber crystals ferment quickly to form as a liquid composite containing the medical amber crystals and paddies; at this time, debris of the medial amber crystals and paddies sunk at on a bottom side of an interior of the bottle are removed; only the composite at an upper side is remained;

clearing and filtering the composite within the bottle; in that the bottle is evaporated through 3 to 10 hours so that the liquid composite is distilled out of the bottle to form as an extracted liquid of the medical amber crystals and the paddies with water therein (step 106). The extracting liquid contains amber cream and nutrient of the paddies, and thus it has plentiful of vitamins A and E, tocopherols, etc., which are usable in skin care so as to provide elasticity to skins. Thus the wrinkles on the face will be flattened. Thus, the present invention is suitable as a skin base in making up. The present invention can be absorbed directly and can be coated on the skin directly to have a preferred treatment effect.

In the present invention, the manufacturing process is developed and tested many times by the inventor of the present invention for a long time period; and the process and environment are built by a long term experiments so as to get a preferred hydrophilic extracted liquid of medical amber crystals. In that the medical amber crystals are resolved in water.

In the present invention, the complicated process and strictly operation environment are provided so that original great molecular groups of medical amber crystals are decomposed into hydrophilic extracted liquid of medical amber crystals plentiful of water and having small molecular groups, which can be directly coated on skin without mixing with water and added with grease or oil. The defect in the prior art medical amber crystals is overcome. The present invention has overcome the defect of the conventional medical amber crystals, which can be resolved in water. Therefore, the usages of the medical amber crystals are widened.

The present invention is thus described; it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for making amber crystals consisting essentially of:
   a) disinfecting and sterilizing natural amber crystals in a bamboo basin wherein a water pan is below the basin;
   b) polishing and cleaning the disinfected and sterilized amber crystals, wherein the amber crystals are cracked into a plurality of small pieces; and then removing impurities and insect corpses therefrom;
   c) preparing a treating liquid which contains tartaric acid, pine root, alcohol and pure water;
   d) placing the amber crystals and the treating liquid from step c) into a bottle for a predetermined time period so that the amber crystals and the treating liquid in the bottle ferment and decompose which causes the molecule groups in the amber crystals to be decomposed into small pieces which then forms a cream-like liquid;
   e) placing rice paddies also into the bottle; sealing the bottle; wherein the bottle is kept in this state for several months so that the amber crystals ferment quickly to form a liquid composite containing the amber crystals and rice paddies wherein the debris of the amber crystals and rice paddies sink to the bottom of the bottle and are then removed such that only the liquid composite remains;
   f) filtering the liquid composite within the bottle; wherein the bottle is evaporated for several hours so that only the amber crystals and the rice paddies remain; and
   g) filtering out the amber crystals.

* * * * *